(12) United States Patent
Koshika et al.

(10) Patent No.: US 6,333,334 B1
(45) Date of Patent: Dec. 25, 2001

(54) USE OF MACROLIDE COMPOUNDS FOR THE TREATMENT OF ARDS

(75) Inventors: Tadatsura Koshika, Nishinomiya; Itsuo Nagatomi, Osaka, both of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/623,595

(22) PCT Filed: Mar. 4, 1999

(86) PCT No.: PCT/JP99/01064
§ 371 Date: Sep. 5, 2000
§ 102(e) Date: Sep. 5, 2000

(87) PCT Pub. No.: WO99/44597
PCT Pub. Date: Sep. 10, 1999

(30) Foreign Application Priority Data

Mar. 6, 1998 (AU) .................................................. PP2231

(51) Int. Cl.$^7$ ............................. A61K 31/00; A61K 31/70
(52) U.S. Cl. ............................................................. 514/291
(58) Field of Search ............................................... 514/291

(56) References Cited

U.S. PATENT DOCUMENTS 5,290,689 * 3/1994 Garrity et al. ........................ 435/119

FOREIGN PATENT DOCUMENTS

WO 92/08474 * 5/1992 (WO).
WO 94/04148 * 3/1994 (WO).

* cited by examiner

*Primary Examiner*—Bruck Kifle
(74) *Attorney, Agent, or Firm*—Oblon, Spivak, McClelland, Maier & Neustadt, P.C.

(57) ABSTRACT

Macrolide compounds, such as the FK506 Substance and its related compounds are provided for the prevention or treatment of adult respiratory distress syndrome. Composition containing such compounds is also disclosed.

5 Claims, No Drawings

USE OF MACROLIDE COMPOUNDS FOR THE TREATMENT OF ARDS

TECHNICAL FIELD

This invention relates to a new use of macrolide compounds for pulmonary diseases. More specifically, this invention relates to a new use of macrolide compounds for preventing or treating adult respiratory distress syndrome (hereinafter, ARDS).

BACKGROUND ART

The ARDS has been recognized as a part of systemic inflammatory response syndrome (SIRS) or multiple organ dysfunction syndromes (MODS). It is a life-threatening inflammatory lung condition characterized by severe acute hypoxemia, respiratory distress and pulmonary edema. In spite of the advances in ventilator and circulation therapy, it is reported that the mortality rate of patients with ARDS still remains high and it exceeds 50%.

Recently, no selective pharmacotherapy is available for ARDS. At present, in a clinical use, glucocorticoid anti-inflammatory steroids, which are very potent immunosuppressive agents, have not proved to be beneficial (TiPS, 14:436–441, 1993). Even high-dose glucocorticoid therapy of patients at risk of developing ARDS neither improved the clinical outcome nor reversed ARDS progression (Chest. 103:932–943, 1993).

DISCLOSURE OF INVENTION

The inventors of this invention have surprisingly found that the macrolide compounds mentioned here-in-below are useful for preventing or treating ARDS.

Accordingly, this invention provides a new use of the macrolide compounds for preventing or treating ARDS.

Further, this invention provides a prophylactic or therapeutic agent for ARDS, which comprises the macrolide compounds.

Still further, this invention provides a method for preventing or treating ARDS, which comprises administering said macrolide compounds to mammals.

As a particular example of the macrolide compounds, the tricyclic compound of the following formula (I), or its pharmaceutically acceptable salt, can be exemplified.

(I)

(wherein each of adjacent pairs of $R^1$, and $R^2$, $R^3$ and $R^4$, and $R^5$ and $R^6$ independently
  (a) is two adjacent hydrogen atoms, but $R^2$ may also be an alkyl group or
  (b) may form another bond formed between the carbon atoms to which they are attached;
$R^7$ is a hydrogen atom, a hydroxy group, a protected hydroxy group, or an alkoxy group, or an oxo group together with $R^1$;
$R^8$ and $R^9$ are independently a hydrogen atom or a hydroxy group;
$R^{10}$ is a hydrogen atom, an alkyl group, an alkyl group substituted by one or more hydroxy groups, an alkenyl group, an alkenyl group substituted by one or more hydroxy groups, or an alkyl group substituted by an oxo group;
X is an oxo group, (a hydrogen atom and a hydroxy group), (a hydrogen atom and a hydrogen atom), or a group represented by the formula —CH$_2$O—;
Y is an oxo group, (a hydrogen atom and a hydroxy group), (a hydrogen atom and a hydrogen atom), or a group represented by the formula N—NR$^{11}$R$^{12}$ or N—OR$^{13}$;
$R^{11}$ and $R^{12}$ are independently a hydrogen atom, an alkyl group, an aryl group or a tosyl group;
$R^{13}$, $R^{14}$, $R^{15}$, $R^{16}$, $R^{17}$, $R^{18}$, $R^{19}$, $R^{22}$ and $R^{23}$ are independently a hydrogen atom or an alkyl group;
$R^{24}$ is an optionally substituted ring system which may contain one or more heteroatoms;
n is an integer of 1 or 2; and
in addition to the above definitions, Y, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkoxy, a benzyl, a group of the formula —CH$_2$Se(C$_6$H$_5$), and an alkyl substituted by one or more hydroxy groups.

Preferable $R^{24}$ may be cyclo(C$_{5-7}$)alkyl group, and the following ones can be exemplified.
(a) a 3,4-di-oxo-cyclohexyl group;
(b) a 3-R$^{20}$-4-R$^{21}$-cyclohexyl group, in which
$R^{20}$ is hydroxy, an alkoxy group, an oxo group, or a —OCH$_2$OCH$_2$CH$_2$OCH$_3$ group, and
$R^{21}$ is hydroxy, —OCN, an alkoxy group, a heteroaryloxy which may be substituted by suitable substituents, a —OCH$_2$OCH$_2$CH$_2$OCH$_3$ group, a protected hydroxy group, chloro, bromo, iodo, aminooxalyloxy, an azido group, p-tolyloxythiocarbonyloxy, or $R^{25}R^{26}$CHCOO—,
in which
$R^{25}$ is optionally protected hydroxy or protected amino, and
$R^{26}$ is hydrogen or methyl, or
$R^{20}$ and $R^{21}$ together form an oxygen atom in an epoxide ring; or
(c) cyclopentyl group substituted by methoxymethyl, optionally
protected hydroxymethyl, acyloxymethyl (in which the acyl moiety optionally contains either a dimethylamino group which may be quaternized, or a carboxy group which maybe esterified), one or more amino and/or hydroxy groups which may be protected, or aminooxalyloxymethyl. A preferred example is a 2-formyl-cyclopentyl group.

The definitions used in the above general formula (I) and the specific and preferred examples thereof are now explained and set forth in detail.

The term "lower" means, unless otherwise indicated, a group having 1 to 6 carbon atoms.

Preferable examples of the "alkyl groups" and an alkyl moiety of the "alkoxy group" include a straight or branched chain aliphatic hydrocarbon residue, for example, a lower alkyl group such as methyl, ethyl, propyl, isopropyl, butyl, isobutyl, pentyl, neopentyl and hexyl.

Preferable examples of the "alkenyl groups" include a straight or branched chain aliphatic hydrocarbon residue having one double-bond, for example, a lower alkenyl group such as vinyl, propenyl (e.g., allyl group), butenyl, methylpropenyl, pentenyl and hexenyl.

Preferable examples of the "aryl groups" include phenyl, tolyl, xylyl, cumenyl, mesityl and naphthyl.

Preferable protective groups in the "protected hydroxy groups" and the "protected amino" are 1-(lower alkylthio)-(lower)alkyl group such as a lower alkylthiomethyl group (e.g., methylthiomethyl, ethylthiomethyl, propylthiomethyl, isopropylthiomethyl, butylthiomethyl, isobutylthiomethyl, hexylthiomethyl, etc.), more preferably $C_1$–$C_4$ alkylthiomethyl group, most preferably methylthiomethyl group;

trisubstituted silyl group such as a tri(lower)alkylsilyl (e.g., trimethylsilyl, triethylsilyl, tributylsilyl, tert-butyldimethylsilyl, tri-tert-butylsilyl, etc.) or lower alkyl-diarylsilyl (e.g., methyldiphenylsilyl, ethyldiphenylsilyl, propyldiphenylsilyl, tert-butyldiphenylsilyl, etc.), more preferably tri($C_1$–$C_4$) alkylsilyl group and $C_1$–$C_4$alkyldiphenylsilyl group, most preferably tert-butyldimethylsilyl group and tert-butyldiphenylsilyl group; and an acyl group such as an aliphatic, aromatic acyl group or an aliphatic acyl group substituted by an aromatic group, which are derived from a carboxylic acid, sulfonic acid or carbamic acid.

Examples of the aliphatic acyl groups include a lower alkanoyl group optionally having one or more suitable substituents such as carboxy, e.g., formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.; a cyclo(lower)alkoxy(lower) alkanoyl group optionally having one or more suitable substituents such as lower alkyl, e.g., cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.; a camphorsulfonyl group; or a lower alkylcarbamoyl group having one or more suitable substituents such as carboxy or protected carboxy, for example, carboxy(lower)alkylcarbamoyl group (e.g., carboxymethylcarbamoyl, carboxyethylcarbamoyl, carboxypropylcarbamoyl, carboxybutylcarbamoyl, carboxypentylcarbamoyl, carboxyhexylcarbamoyl, etc.), tri-(lower)alkylsilyl(lower)alkoxycarbonyl(lower) alkylcarbamoyl group (e.g., trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.) and so on.

Examples of the aromatic acyl groups include an aroyl group optionally having one or more suitable substituents such as nitro, e.g., benzoyl, toluoyl, xyloyl, naphthoyl, nitrobenzoyl, dinitrobenzoyl, nitronaphthoyl, etc.; and an arenesulfonyl group optionally having one or more suitable substituents such as halogen, e.g., benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.

Examples of the aliphatic acyl groups substituted by an aromatic group include ar(lower)alkanoyl group optionally having one or more suitable substituents such as lower alkoxy or trihalo(lower)alkyl, e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.

More preferable acyl groups among the aforesaid acyl groups are $C_1$–$C_4$ alkanoyl group optionally having carboxy, cyclo($C_5$–$C_6$)alkoxy($C_1$–$C_4$)alkanoyl group having two ($C_1$–$C_4$)alkyls at the cycloalkyl moiety, camphorsulfonyl group, carboxy($C_1$–$C_4$)alkylcarbamoyl group, tri($C_1$–$C_4$) alkylsilyl($C_1$–$C_4$)alkoxycarbonyl($C_1$–$C_4$)alkylcarbamoyl group, benzoyl group optionally having one or two nitro groups, benzenesulfonyl group having halogen, or phenyl ($C_1$–$C_4$)alkanoyl group having $C_1$–$C_4$alkoxy and trihalo ($C_1$–$C_4$)alkyl group. Among these, the most preferable ones are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Preferable examples of the "5- or 6-membered nitrogen, sulfur and/or oxygen containing heterocyclic ring" include a pyrrolyl group and a tetrahydrofuryl group.

The tricyclic compounds (I) and its pharmaceutically acceptable salt for use in accordance with this invention are well known to have excellent immunosuppressive activity, antimicrobial activity and other pharmacological activities and, as such, be of value for the treatment or prevention of rejection reactions by transplantation of organs or tissues, graft-vs-host diseases, autoimmune diseases, and infectious diseases [EP-A-0184162, EP-A-0323042, EP-A-423714, EP-A-427680, EP-A-465426, EP-A-480623, EP-A-532088, EP-A-532089, EP-A-569337, EP-A-626385, WO89/05303, WO93/05058, WO96/31514, WO91/13889, WO91/19495, WO93/5059, etc., the disclosures of which are incorporated herein by reference.

Particularly, the compounds which are designated as FR900506 (=FK506), FR900520 (ascomycin), FR900523, and FR900525 are products produced by microorganisms of the genus Streptomyces, such as *Streptomyces tsukubaensis* No. 9993 [deposited with National Institute of Bioscience and Human Technology Agency of Industrial Science and Technology (formerly Fermentation Research Institute Agency of Industrial Science and Technology ), at 1–3, Higashi 1-chome, Tsukuba-shi, Ibaraki, Japan, date of deposit Oct. 5, 1984, accession number FERM BP-927] or *Streptomyces hygroscopicus* subsp. *yakushimaensis* No. 7238 [deposited with National Institute of Bioscience and Human Technology Agency of Industrial Science and Technology (formerly Fermentation Research Institute Agency of Industrial Science and Technology), at 1–3, Higashi 1-chome, Tsukuba-shi, Ibaraki, Japan, date of deposit Jan. 12, 1985, accession number FERM BP-928] [EP-A-0184162]. The FK506 Substance (general name: tacrolimus) of the following chemical formula, in particular, is a representative compound.

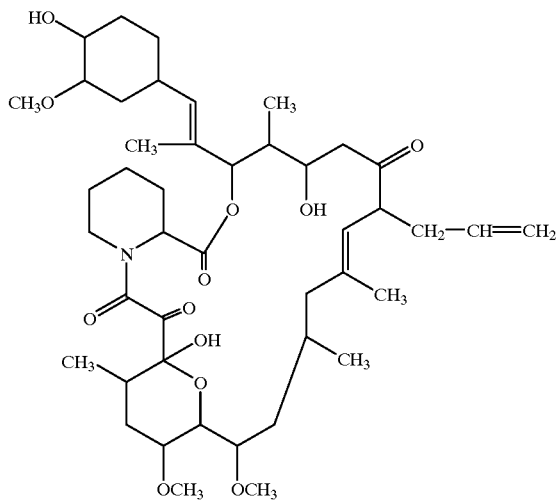

Chemical name: 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The preferred examples of the tricyclic compounds (I) are the ones, wherein each of adjacent pairs of $R^3$ and $R^4$ or $R^5$ and $R^6$ independently form another bond formed between the carbon atoms to which they are attached;

each of $R^8$ and $R^{23}$ is independently a hydrogen atom;

$R^9$ is a hydroxy group;

$R^{10}$ is a methyl group, an ethyl group, a propyl group or an allyl group;

X is (a hydrogen atom and a hydrogen atom) or an oxo group;

Y is an oxo group;

each of $R^{14}$, $R^{15}$, $R^{16}$, $R^{17}$, $R^{18}$, $R^{19}$, and $R^{22}$ is a methyl group;

$R^{24}$ is a 3-$R^{20}$-4-$R^{21}$-cyclohexyl group, in which $R^{20}$ is hydroxy, an alkoxy group, an oxo group, or a —OCH$_2$OCH$_2$CH$_2$OCH$_3$ group, and $R^{21}$ is hydroxy, —OCN, an alkoxy group, a heteroaryloxy which may be substituted by suitable substituents, a —OCH$_2$OCH$_2$CH$_2$OCH$_3$ group, a protected hydroxy group, chloro, bromo, iodo, aminooxalyloxy, an azido group, p-tolyloxythiocarbonyloxy, or $R^{25}R^{26}$CHCOO—, in which $R^{25}$ is optionally protected hydroxy or protected amino, and $R^{26}$ is hydrogen or methyl, or $R^{20}$ and $R^{21}$ together form an oxygen atom in an epoxide ring; and n is an integer of 1 or 2.

The most preferable tricyclic compounds (I) is, in addition to FK506, ascomycin derivatives such as halogenated-ascomycin (e.g., 33-epi-chloro-33-desoxyascomycin), which is disclosed in EP 427,680, example 66a.

As the other preferable example of the macrolide compounds, rapamycin [THE MERCK INDEX (12th edition), No. 8288] and its derivatives can be exemplified. Preferred example of the derivatives is an O-substituted derivative in which the hydroxy in position 40 of formula A illustrated at page 1 of WO 95/16691, incorporated herein by reference, is replaced by —OR$_1$ in which R$_1$ is hydroxyalkyl, hydroalkoxyalkyl, acylaminoalkyl and aminoalkyl; for example 40-O-(2-hydroxy)ethyl-rapamycin, 40-O-(3-hydroxy)propyl-rapamycin, 40-O-[2-(2-hydroxy)ethoxy]ethyl-rapamycin and 40-O-(2-acetaminoethyl) rapamycin. These O-substituted derivatives may be produced by reacting rapamycin (or dihydro or deoxo-rapamycin) with an organic radical attached to a leaving group (for example RX where R is the organic radical which is desired as the O-substituent, such as an alkyl, allyl, or benzyl moiety, and X is a leaving group such as CCl$_3$C(NH)O or CF$_3$SO$_3$) under suitable reaction conditions. The conditions may be acidic or neutral conditions, for example in the presence of an acid like trifluoromethanesulfonic acid, camphorsulfonic acid, p-toluenesulfonic acid or their respective pyridinium or substituted pyridinium salts when X is CCl$_3$C(NH)O or in the presence of a base like pyridine, a substituted pyridine, diisopropylethylamine or pentamethylpiperidine when X is CF$_3$SO$_3$. The most preferable one is 40-O-(2-hydroxy)ethyl rapamycin, which is disclosed in WO94/09010, the disclosure of which is incorporated herein by reference.

The tricyclic compounds (I), and rapamycin and its derivatives, have a similar basic structure, i.e., tricyclic macrolide structure, and at least one of the similar biological properties (for example, immunosupressive activity).

The tricyclic compounds (I), and rapamycin and its derivatives, may be in a form of its salt, which includes conventional non-toxic and pharmaceutically acceptable salt such as the salt with inorganic or organic bases, specifically, an alkali metal salt such as sodium salt and potassium salt, an alkali earth metal salt such as calcium salt and magnesium salt, an ammonium salt and an amine salt such as triethylamine salt and N-benzyl-N-methylamine salt.

With respect to the macrolide compounds usable in the present invention, it is to be understood that there may be conformers and one or more stereoisomers such as optical and geometrical isomers due to asymmetric carbon atom(s) or double bond(s), and such conformers and isomers are also included within the scope of the present invention. And further, the macrolide compounds can be in the form of a solvate, which is included within the scope of the present invention. The solvate preferably include a hydrate and an ethanolate.

The macrolide compounds usable in the present invention may be administered as pure compounds or mixtures of compounds or preferably, in a pharmaceutical vehicle or carrier.

The pharmaceutical compositions of this invention can be used in the form of a pharmaceutical preparation, for example, in solid, semisolid or liquid form, which contains the macrolide compounds of the present invention, as an active ingredient, in admixture with an organic or inorganic carrier or excipient suitable for external(topical), enteral, intravenous, intramuscular, or parenteral applications. The active ingredient may be compounded, for example, with the usual non-toxic, pharmaceutically acceptable, carriers for tablets, pellets, capsules, eye drops, suppositories, solutions (saline, for example), emulsion, suspensions (olive oil, for example), ointment and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an effective amount sufficient to produce the desired effect upon the process or condition of the disease.

Mammals which may be treated using the method of the present invention include livestock mammals such as cows, horses, etc., domestic animals such as dogs, cats, rats, etc. and humans.

While the dosage of therapeutically effective amount of the macrolide compounds varies from and also depends upon the age and condition of each individual patient to be treated, a daily dose of about 0.0001–1000 mg, preferably 0.001–500 mg and more preferably 0.01–100 mg of the active ingredient is generally given for treating diseases, and an average single dose of about 0.001–0.01 mg, 0.2–0.5 mg, 1 mg, 5 mg, 10 mg, 50 mg, 100 mg, 250 mg and 500 mg is generally administered. Daily doses for chronic administration in humans will be in the range of about 0.1–0.3 mg/kg/day. Most preferably, the macrolide compounds can be administered to humans by intravenously in proper forms for such administration.

The following examples illustrate the present invention in further detail, it being to be understood that those examples are not intended to limit the scope of the invention.

EXAMPLE 1

| | |
|---|---|
| FK 506 Substance | 1 g |
| Hydroxypropyl methylcellulose 2910 (TC-5R) | 1 g |
| Lactose | 2 g |
| Croscarmellose sodium (Ac-Di-Sol) | 1 g |

The FK 506 Substance (1 g) was dissolved in ethanol (10 ml), and thereto was added hydroxypropyl methylcellulose 2910 (TC-5R) (1 g) to prepare a suspension. To this suspension was added dichloromethane (5 ml) to prepare a homogeneous solution. Lactose (2 g) and croscarmellose sodium (Trade Mark: Ac-Di-Sol, maker: Asahi Chemical Industry) were homogeneously suspended to this solution, and then the organic solvent was removed by evaporation. The residual product was dried under reduced pressure for 10 hours by vacuum dryer, milled for 2 minutes by coffee mill and then passed through a sieve (32 mesh) to give the solid dispersion composition of FK 506 Substance (5 g). This composition was capsulated by a conventional manner to provide capsules containing 1 mg or 5 mg of FK 506 Substance per each capsule.

EXAMPLE 2

| | |
|---|---|
| FK506 Substance | 10 mg |
| HCO-60 (polyoxyethylenehydrogenated castor oil 60) | 400 mg |
| Ethanol | to 1 ml |

The solution comprising the ingredients stated above is prepared by dissolving the FK506 Substance and HCO-60 in ethanol by a conventional manner. It can be administered via intravenous infusion by diluting with a proper volume of physiological saline.

EXAMPLE 3

The efficacy of FK506 Substance on ARDS-model was evaluated in accordance with the below-mentioned method.

Methods

Fifteen dogs weighing 10.0–15.0 kg were anesthetized with 50 mg/kg of intravenous sodium pentobarbital. After the anesthesia, trachea was exposed and incised, followed by cannulation for artificial ventilation with a mixture of 30% $O_2$ and 70% $N_2$ (tidal volume:180 ml/breath;respiration rate:15–20 breaths/min) and the measurement of airway pressure. Instrumentation included insertions of both bilateral central venous and aortic polyethylene catheters, and introduction of 7F SwanGanz catheter into main pulmonary line. Mean arterial pressure, heart rate, central venous pressure, pulmonary pressure were monitored and recorded continuously. Cardiac output was measured in duplicate using the thermodilution technique. Samples obtained from aortic line, related to various pulmonary functions, such as arterial blood $O_2$ tension ($PaO_2$), hemogrobin oxygen saturation ($sO_2$) and shunt % etc, were analyzed. After the surgical preparation has been completed, the animal was left to stabilize (to ensure arterial carbon dioxide tension: $PaCO_2$; ranging from 35–45 mmHg and pH; from 7.35–7.45) before the start of the study. Heating pads were used to prevent hypothermia. At the end of consecutive experiment, the animals were killed with hemorrhage and left lung was used to determine both lung wet and dry ratio. All animals receiving intravenous administration of 0.5 mg/kg of Lipopolysaccharide (LPS) and 30 $\mu$g/kg of Phorbol myristate acetate (PMA) were divided into 3 groups. In the first group of 5 animals receiving LPS and PMA (served as control), saline was infused throughout the study. In the second group of 5 animals, Methylprednisolone (MP) was given intravenously as an infusion (30 mg/kg) for 30 min soon after LPS/PMA injection. In the third group, FK506 Substance was given intravenously as an infusion (0.025 mg/kg/hr) starting 30 min prior to LPS/PMA injection and continued throughout the duration of the experiment (until 6 h post-LPS/PMA injection). Measurement of each hemodynamic parameter and analysis of arterial and venous blood gas were performed in every hour after the LPS/PMA administration. Each lung sample from left lower lobe was placed in container, weighed immediately after being taken out, and then dried in an oven (Sanyo, TSE) at 105° C. for 24 h. Then, the dry tissue weight was measured. W/D ratio calculated to evaluate the degree of lung edema. W/D ratio was estimated as follows;

W/D ratio=net wet weight of lung/net dry weight of lung. All data are presented as mean±standard error (S.E.). ANOVA and Dunnett's multiple comparison test or Student-t test were applied to access statistical significance between groups. A value of $p<0.05$ were considered as significant differences between groups.

Results

A difference with change in each hemodynamic parameter failed to be perceived among all 3 groups. Although in respect of each parameter related to pulmonary function there was a similar change in control and MP group, there was the marked improvement of $PaO_2$, $sO_2$ and shunt % in FK 506 Substance. Moreover, lung wet/dry ratio in FK 506 Substance tended to decrease (5.22±0.23), in contrast to that in control (6.46±0.85) and MP (7.84±0.75) group. Treatment with FK 506 Substance led to reverse the above ratio dose-dependently.

The above results indicate that the macrolides compounds such FK506 Substance have therapeutic effect against ARDS, and/or acute lung injury.

The patents, patent applications and publications cited herein are incorporated by reference.

We claim:

1. A method for treating an inflammatory lung condition characterized by pulmonary edema which comprises administering a tricyclic compound of the following formula (I):

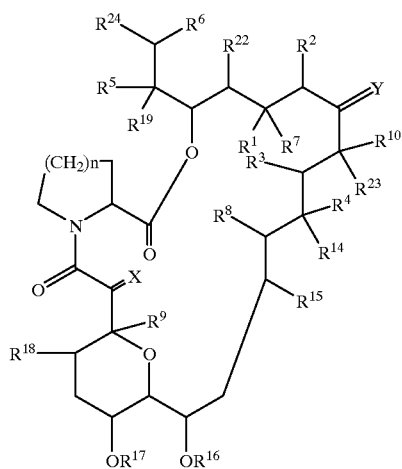

(I)

wherein each of adjacent pairs of $R^1$ and $R^2$, $R^3$ and $R^4$, and $R^5$ and $R^6$ independently
  (a) is two adjacent hydrogen atoms, but $R^2$ may also be an alkyl group or
  (b) may form another bond formed between the carbon atoms to which they are attached;

$R^7$ is a hydrogen atom, a hydroxy group, a protected hydroxy group selected from the group of 1-(lower alkylthio)-(lower)alkyl group, tri(lower)alkylsilyl group, aliphatic acyl group and aromatic acyl groups, or an alkoxy group, or an oxo group together with $R^1$;

$R^8$ and $R^9$ are independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups, or an alkyl group substituted by an oxo group;

X is an oxo group; a hydrogen atom and a hydroxy group; a hydrogen atom and a hydrogen atom; or a group represented by the formula —$CH_2O$—;

Y is an oxo group; a hydrogen atom and a hydroxy group; a hydrogen atom and a hydrogen atom; or a group represented by the formula =N—$NR^{11}R^{12}$ or =N—$OR^{13}$;

$R^{11}$ and $R^{12}$ are independently a hydrogen atom, an alkyl group, an aryl group or a tosyl group;

$R^{13}$, $R^{14}$, $R^{15}$, $R^{16}$, $R^{17}$, $R^{18}$, $R^{19}$, $R^{22}$ and $R^{23}$ are independently a hydrogen atom or an alkyd group;

$R^{24}$ is an optionally substituted cyclo($C_{5-7}$)alkyl group;

n is an integer of 1 or 2; and in addition to the above definitions, Y, R and $R^{23}$, together with the carbon atoms to which they are attached, may represent a saturated or unsaturated 5- or 6-membered one nitrogen, sulfur or oxygen containing heterocyclic ring optionally substituted by one or more groups selected from the group consisting of an alkyl, a hydroxy, an alkoxy, a benzyl, a group of the formula —$CH_2Se(C_6H_5)$, and an alkyl substituted by one or more hydroxy groups; or its pharmaceutically acceptable salt, to a mammal.

2. The method of claim 1, wherein said inflammatory lung condition is adult respiratory distress syndrome.

3. The method of claim 1, wherein said tricyclic compound is FK506 or a FK506 hydrate.

4. A method for treating pulmonary edema, which comprises administering FK506 or a FK506 hydrate to a mammal.

5. The method of claim 1, wherein the heterocyclic ring is a pyrrolyl group or tetrahydrofuryl group.

* * * * *